United States Patent [19]

Elfman et al.

[11] Patent Number: 4,678,057
[45] Date of Patent: Jul. 7, 1987

[54] BREATH ALCOHOL ANALYZER

[75] Inventors: Brian P. Elfman, Alameda; Patricia L. Zajac, Richmond, both of Calif.

[73] Assignee: Autosense Corporation, Hayward, Calif.

[21] Appl. No.: 819,514

[22] Filed: Jan. 16, 1986

[51] Int. Cl.⁴ .......................... B60R 1/00; G08B 23/00
[52] U.S. Cl. ................................... 180/272; 340/52 R
[58] Field of Search ............. 180/272; 340/52 R, 576, 340/561, 562

[56] References Cited

U.S. PATENT DOCUMENTS

| | | | |
|---|---|---|---|
| 3,855,573 | 12/1974 | Honda et al. | 180/272 |
| 4,117,467 | 9/1978 | San | 340/506 |
| 4,507,644 | 3/1985 | Abrahamson | 180/272 |
| 4,565,997 | 1/1986 | Seko et al. | 180/272 |
| 4,613,845 | 9/1986 | Du Bois | 180/272 |

*Primary Examiner*—Richard A. Bertsch
*Attorney, Agent, or Firm*—William H. F. Howard

[57] ABSTRACT

Disclosed is a system, both apparatus and method, for analyzing a breath sample (22). A transducer (24) senses the pressure, temperature and humidity of the breath sample and in response generates a breath signature signal (26). A sensor (28) detects the alcohol content of the breath sample and in response generates an alcohol signal (30). Also included is a breath reference (32), and an alcohol reference (34) which includes an alcohol threshold level (36). A first comparator (38) compares the breath signature signal with the breath reference, and in response generates either a valid signal (40) if the signals substantially match or an invalid signal (44) if the signals do not substantially match. A second comparator compares the alcohol signal with the alcohol reference, and in response generates either a passing signal or a failing signal depending on whether or not the threshold level is exceeded. In this Abstract, the parethetical reference numerals are included only to facilitate rapid understanding, and not to define or scope the Invention defined by the claims.

53 Claims, 6 Drawing Figures

BREATH ALCOHOL ANALYZER

FIELD OF THE INVENTION

This Invention relates generally to systems for analyzing breath samples of humans. More particularly, this Invention relates to systems employing a person's breath sample to develop both a (1) breath signature signal for identifying certain characteristics of the person and (2) an alcohol signal produced by detecting the presence of alcohol.

BACKGROUND OF THE INVENTION

Various schemes have been devised for analyzing human breath samples to obtain information about a person, particularly information relating to the person's percent blood alcohol concentration (BAC). However, shortcomings and deficiencies still exist in the technology.

Specifically, existing breath analysis techniques simply do not provide approaches for gathering information other than BAC about the person from a breath sample. Examples of existing technology are discussed below.

U.S. Pat. No. 4,093,945 to Collier et al discloses a breath testing system for alcohol intoxication breath testing. The system includes (1) a breath input unit, (2) a controller which delivers a sample of deep lung breath to (3) an evaluator including an alcohol detector and an output apparatus. The controller includes a breath flow sensing means to insure that a deep lung breath sample is tested. A passing signal cannot be obtained unless (a) the predetermined continuous and uninterrupted flow has occurred, and (b) the resulting sample tests below a predetermined alcohol concentration.

U.S. Pat. No. 4,316,380 to Heim et al shows means for determining the breath alcohol content of a test person. The system (1) measures the alcohol content of the breath to produce an alcohol content signal, (2) measures the change in the alcohol content signal, (3) measures a flow of the breath of the test person, and (4) indicates the alcohol content using the alcohol content signal only when the change in the signal per unit time is below a pre-selected change value and the flow is above a pre-selected flow value, and further where the flow has not dropped below the predetermined flow value since it first reached the predetermined flow value.

U.S. Pat. No. 4,317,453 to Heim et al discloses a system for testing a person's breath for the determination of its alcohol content. The system first determines when the breathing air is at a condition in which breath testing results will be effected. This is done by arranging a capacitor in a breathing tube through which the breathing air is detected.

First, the capacitor is heated to a predetermined temperature. Then the breathing air is directed over it so as to cool the capacitor until it has attained a predetermined temperature change. This temperature change is such that it will take place when the person's breathing air has its desired consistency.

When this occurs, the breathing air is then directed into a test chamber, in which it is tested to determine the constituency of the breathing air, particularly the percentage of alcohol which it contains. The device for testing the person's breath also contains a test chamber connected to the tube with a control means. This control means senses the temperature of the capacitor and then permits the flow of the gas into the test chamber only after a predetermined temperature drop has occurred.

U.S. patent application with Ser. No. 494,301, filed May 13, 1983 by Brian P. Elfman and Lawrence T. Rojahn, now abandoned, discloses an apparatus for measuring the blood alcohol concentration (BAC) of an individual. The apparatus includes (1) a gas vapor sensor for receiving and analyzing the alcohol concentration in the breath of the individual, (2) an analog-to-digital converter, and (3) a gas analyzer for detecting the rate of change of the signal generated by the sensor.

When the rate of change of the signal is at or near zero, thereby indicating the breath is deep lung air, the sensor signal is transposed to a BAC reading in the BAC look-up table. The BAC reading is then compared to a pre-recorded level obtained from a memory, to determine the intoxication level of the individual. A flow sensor can be provided to assure that the individual is expelling a sufficient volume of air to assure a good reading. An auto ignition gate can be provided to disable a vehicle if the individual is found to have a BAC reading above a predetermined level which indicates intoxication.

While the above technology does offer laudible approaches and solutions with respect to the particular situation each addresses, none of them individually or in combination disclose or suggest the Invention defined in the appended Claims of this present case. Specifically, the following problems persist despite the efforts of the existing technology.

All of the above approaches are specifically directed to determining the BAC of a person in order to prevent that person from operating a vehicle if he is inebriated. No additional information can be determined by these systems from the breath sample. These systems are not sophisticated enough to accurately and reliably screen users to ensure that only an authorized person is tested.

Existing breath analyzing equipment, to provide a breath sample test result which can be introduced into evidence in a drunk driving prosecution, (a) must be built to very precise specifications, (b) are large and not easily transportable, and (c) are sensitive and thus require frequent servicing in order to remain precisely calibrated. As a result, the available equipment is quite expensive.

Because the accurate equipment is not easily transportable, an arresting police officer faces a race against time in getting an inebriated person to the equipment's location quickly enough that a person's body does not metabolize the alcohol prior to a BAC test.

Additionally, these systems have difficulty in accurately detecting attempts to deliver bogus breath samples to them, for example in the case where inebriated person #1 has a breath sample delivered by a sober person #2. The opportunity also exists to introduce a bogus breath sample originating in a compressed air bottle or having been filtered prior to being subjected to a BAC test.

These are only a few of the problems which have not been adequately resolved by the existing technology. Because of these problems, it became necessary to devise the Invention (1) disclosed by example below, and (2) defined in the appended claims.

SUMMARY AND ADVANTAGES OF THIS INVENTION

Summary of This Invention

Solutions and advantages are offered by this Invention which resolve many of the deficiencies still present in the existing technology.

Broadly summarized, the Invention is a system for analyzing a breath sample, the apparatus comprising the following six (6) elements:

(1) means for sensing the pressure, the temperature and the humidity of the breath sample and in response generating a breath signature signal;

(2) means for sensing the alcohol content, if any, of the breath sample and in response generating an alcohol signal;

(3) means providing a breath reference;

(4) means providing an alcohol reference which includes an alcohol threshold level;

(5) means for comparing the breath signature signal with the breath reference and in response generating one of (i) a valid signal if the breath signature signal substantially matches within a pre-selected range or envelope and (ii) an invalid signal if the breath reference signal does not substantially match the breath reference within the pre-selected range or envelope; and (6) means for comparing the alcohol signal with the alcohol reference and in response generating one of (i) a passing signal if the alcohol signal is less than the threshold level and (ii) a failing signal if the alcohol signal equals or exceeds the threshold level.

Additional features offered by this Invention, but not summarized above, are (1) described by example below and (2) defined and scoped in the appended claims.

Advantages of This Invention

This Invention expands and improves the technology of breath analysis, to thereby permit the control and acquisition of new and more sophisticated information about the person giving the breath sample.

A key feature and advantage of this Invention is that, on the basis of a single breath sample from a particular person, a breath signature signal can be generated for that particular person.

This Invention employs a simple, sophisticated and inexpensive transducer to measure the temperature, pressure and humidity of a breath sample. The transducer then integrates these values together to produce a single output breath signature signal in the form of a frequency spectrum for the person delivering the sample.

Previously existing technology requires complex apparatus to measure temperature, pressure and temperature together; these values are then manipulated by complex mathematical formulas to obtain information about the breath sample. Complex flow meters are used to ensure delivery of a deep breath sample. The only value measured by existing technology is the BAC, and that is measured with a chemical sensor.

In contrast, this Invention performs a simple joint measurement of temperature, pressure and humidity combined, integrates this measurement, and produces as an output the breath signature signal. This is done in addition to measuring the alcohol in this breath sample.

This Invention is rugged, accurate, reliable, easily calibrated and supplies breath sample information that can be used by the prosecution in a drunk driving adjudication. When installed in a vehicle and interlocked into the vehicle's ignition system, it would be impossible for an inebriated person to start the vehicle.

Other advantages offered by this Invention are described by example below and defined by the appended claims.

DETAILED DESCRIPTION OF EXAMPLE PREFERRED EMBODIMENTS

This Detailed Description, which incorporates the accompanying Drawings briefly described below, offers specific examples (i.e., embodiments) of how to practice the Invention, but it does not actually define the Invention. Instead, the Invention is defined by the numbered paragraphs of the appended claims. This Detailed Description sets forth the best modes presently contemplated by the Inventor for making and using the claimed Invention. Further, this detailed Description is intended for facilitating, through example, the understanding of the Invention defined in the claims.

SYSTEM OVERVIEW: FIG. 1

Figure 1:
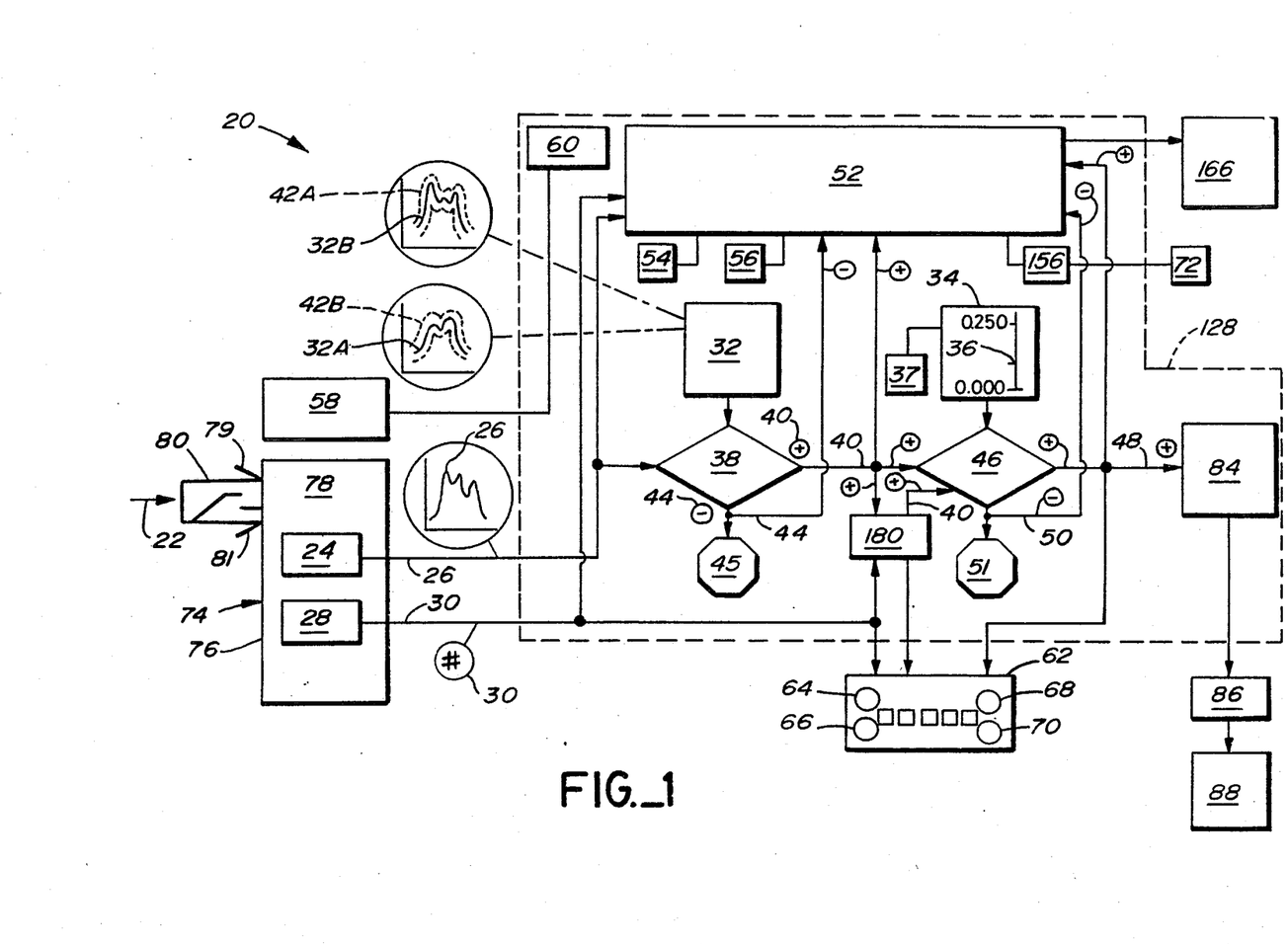
FIG. 1 schematically shows how the Invention processes breath sample information.

FIG. 1 shows an overview of method and apparatus 20 for analyzing a breath sample 22. Included is a first means 24 for sensing the temperature, the pressure and the humidity of the breath sample 22, and in response generating as an output a breath signature signal 26.

Also included is a second means such as sensor 28 for sensing the alcohol content if any of the breath sample 22, and in response generating an alcohol signal.

A third means such as breath reference 32 is stored in computer memory for providing a breath reference. A fourth means, e.g. an alcohol reference 34, is stored in computer memory for providing an alcohol reference and includes an alcohol threshold level 36, in this case established at 0.025% BAC.

A fifth means, for example a first comparator 38, is used for comparing the breath signature signal 26 with the breath reference 32. In response, comparator 38 generates either (1) a valid signal, shown as a plus sign enclosed in a circle and indicated as a "yes" with a reference numerial 40, of the breath signature signal 26 substantially matches within a pre-selected range (shown in FIG. 1 as a passing envelope 42) stored in breath reference 32; or (2) an invalid signal, shown in FIG. 1 as a minus sign enclosed in a circle indicating a "no" and labeled with reference numberial 44, if the breath signature signal 26 does not substantially match the breath reference 32 within the pre-selected range 42.

Finally included is a sixth means, for example a second comparator 46, for comparing the alcohol signal 30 with the alcohol reference 34. In response, comparator 46 generates one of the following: (1) a passing signal shown as a plus sign enclosed in a circle indicating a "yes" and labeled with reference numerial 48, if the alcohol signal 30 is less than the threshold level 36; or (2) a failing signal, shown as a minus sign enclosed in a circle and labeled with a reference numeral 50, if the alcohol signal 30 equals or exceeds the threshold level 36.

System Details

Additional features and structures are offered by this Invention to further enhance its usefulness. The details are fully described below.

Figure 2:
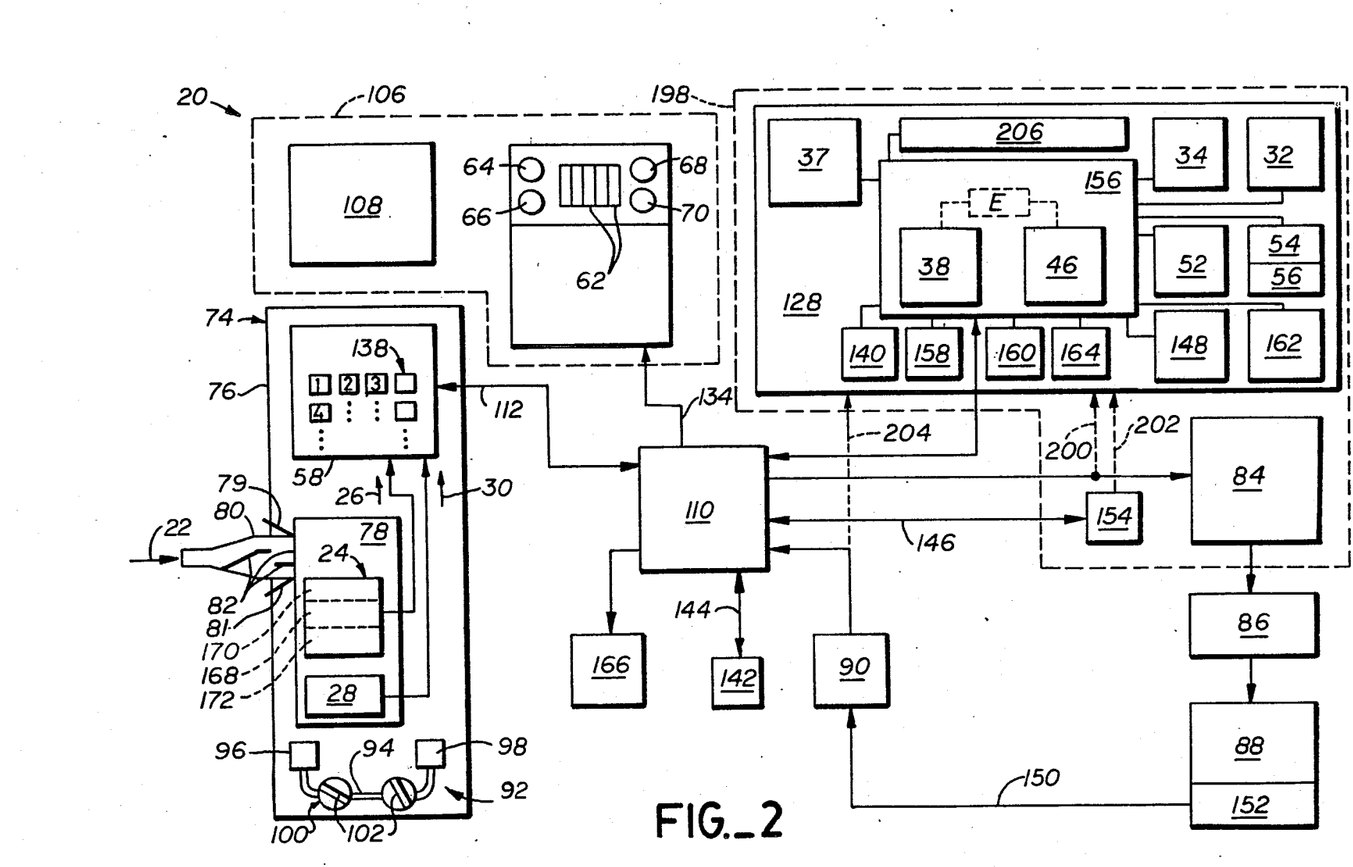
FIG. 2 is a hardware schematic diagram.

FIGS. 1 and 2: Additional Embodiments

The Invention has a seventh means, shown as a computer memory 52, storing certain test results performed by the breath analysis. These test results include the breath signature signal 26, the alcohol signal 30, the response of the fifth means (comparator 38) in comparing the breath signature signal with the breath reference 32, the response of the sixth means (comparator 46) in comparing the alcohol signal with the alcohol reference 34, and the date and time when breath sample 22 was analyzed. A time clock 54 and a date clock 56 provide the respective time and date of the performance of each breath analysis.

Further included can be an eighth means for preventing the use of apparatus 20 by an unauthorized person. In one case, this function is provided by a keyboard 58 having number keys for inputing a Personal Identification Number (PIN). This PIN is coupled to a "recognize PIN" component 60 within the system's controller electronics, for identifying a user as being a valid user. This eighth means is expandable to include use of the validity test results performed by comparator 38 to confirm that a valid breath sample is analyzed by transducer 24 and sensor 28.

The ninth means, for example a digital display unit 62, is employed for numerically displaying alcohol signal 30 and the sixth means (comparator 46) response (i.e., "P" for "Pass" and "F" for "Fail") in comparing alcohol signal 30 with alcohol reference 34.

A grouping of first, second, third and fourth respective status lights 64, 66, 68 and 70 serve as a tenth means for displaying a plurality of status indicators regarding the apparatus 20 and the breath sample 22. The status indicators include a plurality of differently colored lights which variously cycle to being in the states of "steady on", "flashing on", and "steady off."

The colors selected for these lights are red, green, amber and blue. At the beginning of a test sequence, all lights are off. The amber light is then activated into the "flashing on" state; the system is checking itself to make sure that it is operating correctly for taking a test. If the blinking continues, it means a test can be taken, but the system needs to be checked because of some malfunction, for example to replace a power supply. However, if the amber light goes to a "steady on" condition, then the system is malfunctioning and no test can be properly taken. If the system is operating correctly, the amber light will then move to the "steady off" condition to indicate that the system is functioning properly.

Next, the blue light begins blinking, to indicate that apparatus 20 is preparing itself for taking a test. This can take anywhere from about five seconds to about sixty seconds, depending on such conditions as when the last test was taken, the state of the power supply, and the temperature. When the system is ready to accept a test, the blue light changes to the "steady on" condition. Then, at the end of a test, the blue light goes to the "steady off" condition to indicate that a sufficient breath sample has been delivered to permit an adequate test.

If the test passes, then the green light achieves a "steady on" condition. Conversely, if the breath sample fails, the red light cycles to the "steady on" condition.

A power supply 72 serves as an eleventh means for supplying power to the apparatus 20.

A sampler 74 serves as a twelfth means for receiving the breath sample 22. Sampler 74 comprises a housing 76 formed to be grasped in the hand (not shown) of a person, and transported to the mouth (not shown) of the person who is to deliver the breath sample 22, the twelfth means (sampler 74) defining within itself a hollow chamber 78 for receiving the breath sample 22.

Twelfth means 74 further includes a mouthpiece 80 which is removably mountable to the housing 76 to be in fluid communication with the chamber 78. The mouthpiece 80 includes an integral trap 82 for removing moisture and particulate matter (not shown) if any entrained in the breath sample as the breath sample moves from the person toward the chamber 78.

An ignition enable 84 is a switch which functions as a thirteenth means for interlocking the apparatus 20 into a starter system or ignition 86 of an engine 88 of a powered machine. The thirteenth means ignition 84 is formed to prohibit operation of the starter system or ignition 86 unless both of the following occurs: (1) the response generated by the fifth means comparator 38, when comparing the breath signature signal 26 with the breath reference 32, is a valid signal; and (2) the response generated by the sixth means comparator 46, when comparing the alcohol signal 30 with the alcohol reference 34, is a passing signal.

A detector 90 is a fourteenth means for coupling the apparatus 20 to a powered machine or engine 88 to detect one of (1) the machine is operating and (2) the machine is not operating.

Security hardware 92 serves as a fifteenth means for installing the apparatus 20 in a vehicle so the apparatus is accessible for a person to deliver a breath sample while being sufficiently secure to inhibit tampering with the apparatus by the person. A fiber optic cable 94 is coupled between a light emitter 96 and a light receiver 98. These three items are recessed below the surface of sampler 74. Screws 100 are each penetrated by a hole 102 defined in the screw neck. If an attempt is made to unscrew screw 100, hole 102 will pass light through fiber optic cable 94 so detector 98 will indicate that sampler 74 has been breached. This security hardware system 92 can be used to secure all pieces of apparatus 20 into a powered vehicle.

Figure 5:
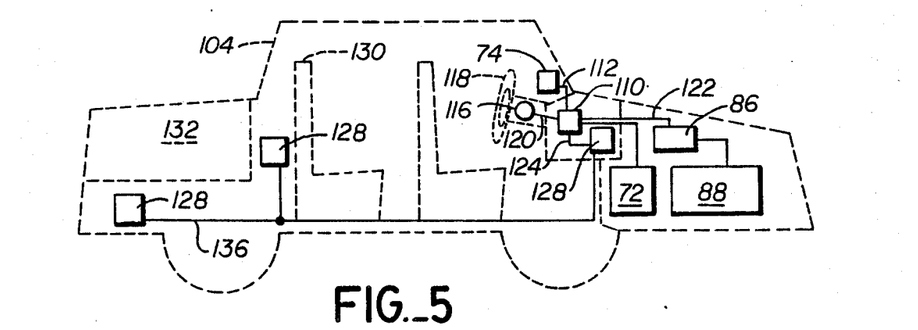
FIGS. 5 and 6 illustrate installation of the inventive apparatus in an automobile.
Figure 6:
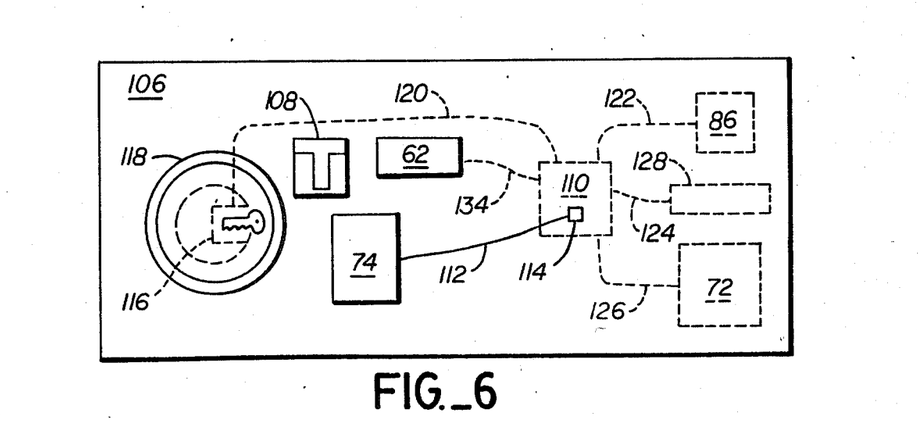

FIGS. 5 and 6 Embodiments

Another means for security installation of the apparatus in a vehicle is to separate the apparatus into sub-systems or components which are isolated from one another. In a vehicle 104, some components are mounted on a dashboard 106, including sampler 74, display 62, and cradle 108 for holding sampler 74 when not in use. In FIG. 5 the components are drawn with solid lines.

Other components are installed behind the dashboard so they are isolated from a user. These components are drawn in FIG. 6 as dashed boxes and dashed lines. A junction box 110 servies as a switch for communicating the components with each other. Sampler 74 is coupled with a visible cable 112 to a port 114 provided to penetrate dashboard 106 for coupling sampler 74 to junction box 110. As is typical, an ignition switch 116, operable by a key, is recessed into the automobile's steering column below a steering wheel 118. A hidden cable 120 couples ignition switch 116 to junction box 110. Hidden cables 122, 124 and 126 respectively connect junction box 110 to ignition 86, the controller electronics 128 for operating apparatus 20, and 72 which in this case is a 12 volt rechargeable automobile battery.

FIG. 5 shows the system components of apparatus 20, and the parts of automobile 104 with which the components interact, as solid lines. As FIG. 5 illustrates, electronics 128 can also be installed behind the rear passenger seat 130 in front of trunk compartment 132. Alternatively, electronics 128 can be installed beneath the floor surface of trunk compartment 132. In FIG. 6, digital display 62 is coupled to junction box 110 through a cable 143. In FIG. 5, a cable 136 would connect respective controller 128 to junction box 110.

FIGS. 1 and 2: Further Embodiments

Keyboard 58 (FIG. 2), besides having number keys typical to hand-held calculators, includes additional button keys 138 labeled respectively with letters A, B and C. These buttons can be reserved for adding additional system features in the future as desired. Presently it is contemplated that one button, for example C, will be provided to permit a user to "clear" an incorrect entry through keyboard 58. In controller 128, a clear circuit 140 will be provided to accomplish this function.

It is contemplated that the FIG. 1 power supply 72 will be implemented as shown in FIG. 2 with a 12 volt DC car battery 142 and a rechargeable standby plus or minus 6 volt DC sealed lead acid battery, respectively coupled through a cable 144 and a cable 146 to junction box 110. The electronics in controller 128 would include a battery control 148 logic that would permit charging of both batteries from engine 88 when detector 90 senses engine 88 is operating. Detector 90 can be coupled, e.g. through a cable 150, to an alternator 152 coupled to engine 88.

The 6 volt SLA battery is labeled with reference numeral 154. Batteries 142 and 154 are interconnected in such a way to each other and to controller 128 so baqtery control 148 ensures that car battery 142 is never connected directly into controller 128. Battery 142 must be electrically isolated from controller 128 so a power surge will not burn up controller 128 or the other electronic components.

Controller 128 electronics include a microprocessor 156, also known as a Central Processing Unit (CPU), for controlling the logical operations. CPU 156 is coupled to a status light control 158 for operating status indicator lights 64, 66, 68 and 70. A breath reference range adjust 160 is included to permit the envelope or range of deviations from the breath reference to be changed, to thereby make the sensitivity of breath reference 32 greater or lesser; the breath signature signal 26 will pass or fail depending on how closely it is forced to match the breath reference.

A personal identification number (PIN) register 162 is coupled to microprocessor 156 for comparison with the PIN keyed in by the user on keyboard 58. A read out control 164 is accessible through microprocessor 156 to print out or otherwise display the memory results 52 to a results read out display 166.

In one construction, transducer 24 comprises a thin film of substantially dielectric material 168 sandwiched between a first electrical conductor 170 and a second electrical conductor 172. For this application, transducer 24 has been fabricated from Kynar Piezo film, a specially processed polyvinylidene flouride (PVDF) that purportedly exhibits the highest piezoelectric and pyroelectric properties of any known plastic. Kynar is a registered trademark of Pennwalt Corporation, 900 First Avenue, King of Prussia, PA, 19406, USA.

Figure 3:
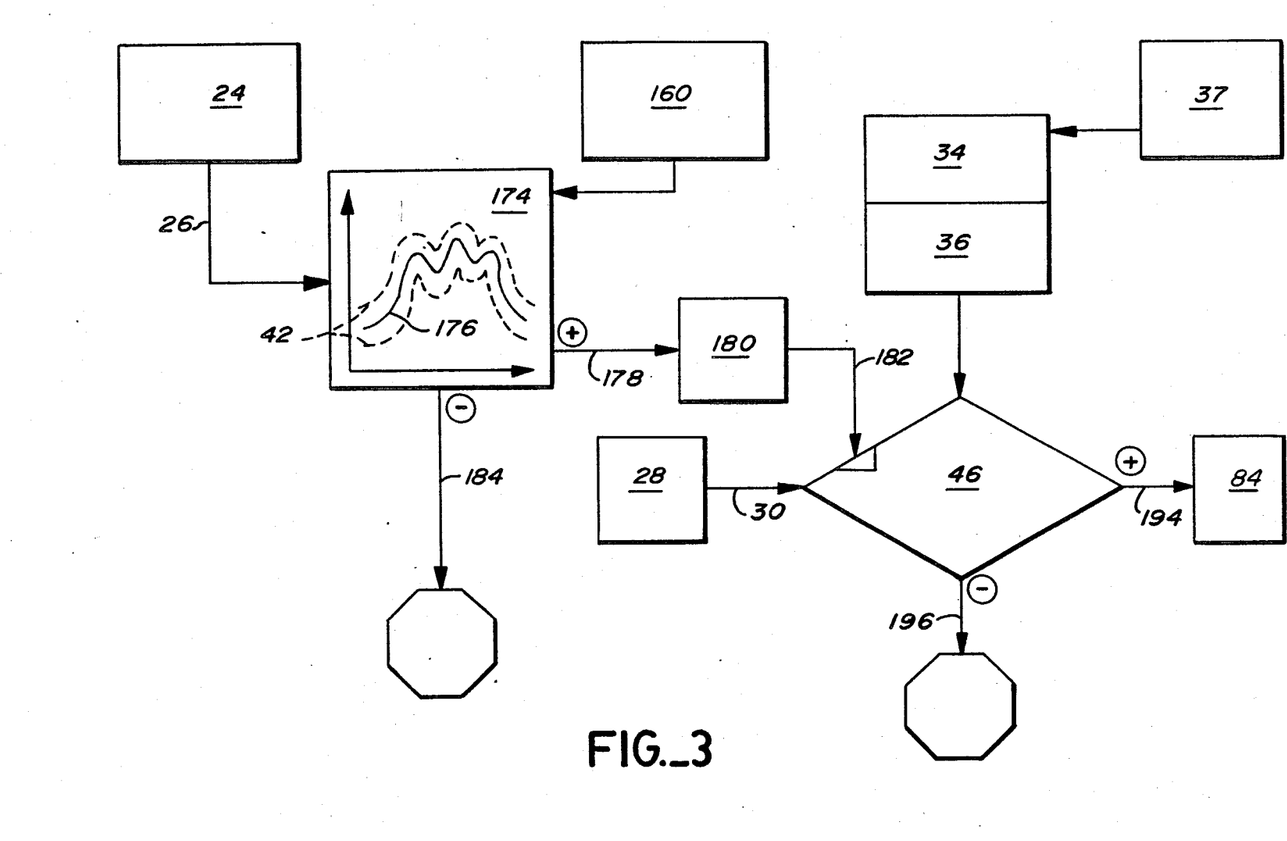
FIG. 3 shows an alternative comparator arrangement.
Figure 4:
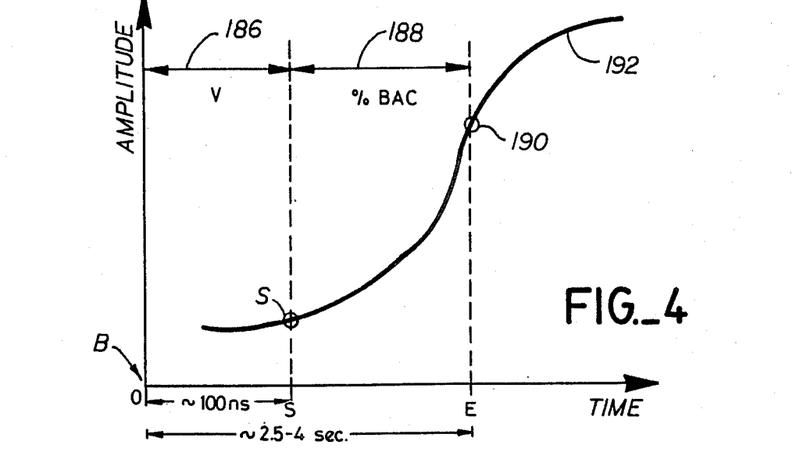
FIG. 4 illustrates breath sample analysis.

FIGS. 3 and 4 Embodiments

FIG. 3 shows an alternative construction of comparators which somewhat differs from the FIG. 1 arrangement of first comparator 38 and second comparator 46.

In FIG. 3, the first comparator is in the form of an electronic filter 174 in which a breath reference 176 having permissible ranges of diviations shown as envelope 42 being stored in filter 174. The sensitivity of filter 174 can be changed with envelope adjust 160 to expand or narrow envelope 42.

In operation, the breath signature signal 26 from transducer 24 is essentially matched against breath reference 176. If signal 26 falls within envelope 42, signal 26 will be seen as a "valid" signal 178. Valid signal 178 trips an enable switch 180, which generates and sends an "okay to test" signal 182 to turn on comparator 46. Second comparator 46 then operates as previously described.

However, if filter 174 determines that signal 26 is invalid, an invalid signal 184 is issued, which causes the system to stop and therefore not permit ignition enable 84 to function. Ignition 86 cannot be operated.

FIG. 4 illustrates the analysis of a breath sample.

Beginning at time equals zero, a person begins breathing into mouthpiece 80. In Region 1, labeled with reference numerial 186, transducer 24 generates breath signature signal 26 for matching in comparator 38 against breath reference 32 to determine whether or not this is a valid sample. In typically less than one second, and on the average within about 100 milliseconds, first comparator 38 makes this determination.

In Region 2, labeled with reference numerial 188, sensor 28 measures the alcohol content of the breath sample and generates alcohol signal 30. At knee 190 of breath curve 192 the sampling is complete. The results are stored in computer memory, and second comparator 46 determines whether or not the breath sample passes. A pass signal is delivered to the ignition enable 84, which permits a vehicle to be started. A fail signal 196 prohibits starting of the vehicle.

On average, about 2.5 to 4.0 seconds will elapse from beginning to end of a test; in some cases my take up to ten (10) or twenty (20) secs. (e.g. someone with emphysema).

As illustrated in FIG. 2, controller electronics 128 can be expanded as shown with dashed line 198 to encompass components which initially are not integral to the controller. For example, ignition interlock control 84, standby battery 154 and detector 90 can be directly coupled to controller 128 through respective cables 200, 202 and 204. With this arrrangement, these components would not be coupled to junction box 110.

In both versions of the controller, a junction box controller is included, shown as reference numerial 206, to permit microprocessor 156 to control the routing function of junction box 110.

FIGS. 1–6: Other Apparatus & Method Embodiments

Viewed from a slightly different standpoint, the Invention offers an apparatus 20 for performing a test of a breath sample 22 delivered to a sampler 74 by a person (1) to determine a measure of the alcohol content if any of the breath sample, and (2) to determine one of (i) the alcohol content is less than a pre-determined threshold level 36 and thus the breath sample is a passing sample and (ii) the alcohol content is greater than the threshold level 36 and thus the breath sample is a failing sample.

The apparatus comprises a first comparator 38 which performs a validity test, to thereby function as a first means for accurately determining the precise moment for starting the measurement of the alcohol content. In less than one second, and typically on the order of about 100 milliseconds, comparator 38 compares breath signature signal 26 with breath reference 32. If this produces a positive result, then breath signature signal 26 is found to be "valid", thus sending a "yes" signal (shown with reference numeral 40) to the enable switch 180. This in turn enables second comparator 46 to commence performing the alcohol threshold "pass-fail" test.

Security hardware 92, previously described, operates as a second means for minimizing tampering with the apparatus 20 by the person in order to prevent the changing of any test result and to prevent damage to the apparatus. Alternatively or additionally, second means can be provided in the form of remotely locating each component of apparatus 20 at various locations in a vehicle, such as behind the dashboard or beneath the floor.

Mouthpiece 80 serves as a third means for providing a hygienic breath sample to sampler 74.

The FIG. 5 separate component installation with the components joined by cabling provides a fourth means for easily installing apparatus 20 to interconnect into ignition system 86 of a vehicle 104. The component of apparatus 20 in combination permit ignition system 86 to be started by the person if the person delivers a passing sample, and does not permit the ignition system to be shut off by the person if the person delivers a failing sample.

The FIG. 6 installation featuring a hand-held portable sampler, and the FIG. 1 arrangement of transducer 24, sensor 28 and controller electronics 128, provide a fifth means for performing the test quickly so no more than about ten seconds time elapses from the beginning to the end of the test. Preferably, however, no more than five seconds will elapse between the time a person delivers a test breath sample to sampler 74 and the time apparatus 20 delivers an ignition enable signal from ignition enable 84 to ignition 86; therefore, a person delivering a passing sample would be able to start an automobile within about five seconds after entering the automobile to start it.

Memory 52 operates as a sixth means for storing the test results to prevent access by the person who delivers the breath sample. However, memory 52 is designed in such a manner that a person authorized to retrieve the test results can do so (i.e. someone monitoring another person's breath sample history). This would allow, for example, for Caseload management by a Probation Officer monitoring the breath sample entry of a person on parole from a drunk driving conviction.

Mouthpiece 80 is provided with spring-loaded latches 79 and 81, provided to positively hold mouthpiece 80 securely in place in sampler 74. Mouthpiece 80 is inexpensive and designed for being disposed of after a single use; this ensures the delivery of hygienic breath samples. Integral trap 82 is provided with an arrangement of vanes for removing moisture and particulate matter entrained in the breath sample.

The system of this Invention, in addition to the apparatus described above, offers a method for analyzing a breath sample 22. This method is comprised of the steps next described below.

Transducer 24 performs the step of sensing the temperature, the pressure and the humidity of the breath sample 22 and in response generating a breath signature signal 26.

Sensor 28 accomplishes the step of sensing the alcohol content if any of the breath sample, and in response generating an alcohol signal 30.

Breath reference 32 serves to do the step of providing a breath reference. Likewise, alcohol reference 36 performs the step of providing an alcohol reference which includes an alcohol threshold level 36, which can be changed as desired using threshold level adjuster 37.

First comparator 38 accomplishes the step of comparing the breath signature signal 26 with the breath reference 32, and in response generating one of the following: (i) a valid signal 40 if the breath signature signal 26 substantially matches within a pre-selected range (passing envelopes 42A and 42B) the breath reference signals (32A and 32B); or (ii) an invalid signal 44 if the breath signature signal 26 does not substantially match the breath reference in the pre-selected range.

Finally, the second comparator 46 performs the step of comparing the alcohol signal 30 with the alcohol reference 34 in the response generating one of the following: (i) a passing signal 48 if the alcohol signal 30 is less than the threshold level 36; or (ii) a failing signal 50 if the alcohol signal 30 equals or exceeds the threshold level 36.

As can be seen in FIG. 1, a "yes" signal such as 40 and 48, shown as a plus sign enclosed in a circle, indicates the desirable condition; that is, signal 40 shows the breath signature signal 26 has passed the validity test performed in comparator 38. Conversely, the undesirable condition is indicated by a "no" as with signals 44 and 48, shown as a minus sign enclosed in a circle; for example, signal 44 shows that breath signature signal 26 did not pass the validity test performed in comparator 38. The "no" signals 44 and 50 respectively cause a system stop as at stop 45 and stop 51.

Threshold level 36 is shown in FIG. 1 to be set at 0.025% BAC on a scale ranging from a low of 0.00% VAC to a high of 0.25% BAC. This low-high range can be expanded; likewise it can be made sensitive to thousandths of a percent BAC. Further, threshold level adjust 37 can be used to change threshold level 36 to be anywhere on the low-high scale. The 0.025% BAC level is sufficiently below 0.10% BAC, the legal definition of being under the influence of alcohol, to protect the public and vehicle operators.

The expression "deep lung air" is synonymous with "alveolar air" as defined in U.S. Pat. No. 4,316,380 to Heim, referenced above. This is the portion of air delivered from deep in a person's lung; it is this air that is measured in order to determine a person's % BAC. This "deep lung air" is to be distinguished from the air delivered from a person's oral cavity and pharylingeal cavity.

Memory 52 (FIGS. 1 and 2) record test results including the mere fact that a breath sample was delivered to be analyzed and the total number of samples taken.

The breath signature signal 26 produced by transducer 24 is in the form of a frequency spectrum.

INCORPORATION BY REFERENCE: OTHER PATENT APPLICATIONS

The following U.S. patent applications are hereby incorporated by reference into this present application, and form a part of this application:

application of Brian P. Elfman and Lawrence R. Rojahn, Ser. No. 494,301, filed May 13, 1983, entitled "Device to Prevent Drunken Driving", now abandoned;

application of Brian P. Elfman, Ser. No. 787,266, filed Oct. 15, 1985, for "A System for Detecting Tampering", now pending;

application of Brian P. Elfman, Ser. No. 791,327, filed Oct. 25, 1985, for "System for Breath Signature Characterization", now pending;

application for Brian P. Elfman et al, Ser. No. 813,246, filed Dec. 24, 1985, for a design entitled "Mouthpiece", now pending; and application of Brian P. Elfman et al, Ser. No. 813,058, filed Dec. 24, 1985 for "Integrated Mouthpiece and Moisture Trap", now pending.

CLAIMS DEFINE THE INVENTION

The examples discussed above in the Detailed Description illustrate only a few of the constructions and methods possible according to this Invention. However, it is to understood that the following numbered Claims both (1) define the Invention and (2) establish the scope of the Invention.

The invention claimed is:

1. An apparatus for analyzing a breath sample, comprising:
    (a) a first means for sensing the pressure, the temperature and the humidity of the breath sample and in response generating a breath signature signal;
    (b) a second means for sensing the alcohol content if any of the breath sample and in response generating an alcohol signal;
    (c) a third means for providing a breath reference;
    (d) a fourth means for providing an alcohol reference which includes an alcohol threshold level;
    (e) a fifth means for comparing the breath signature signal with the breath reference and in response generating one of (i) a valid signal if the breath signature signal substantially matches within a pre-selected range the breath reference and (ii) an invalid signal if the breath signature signal does not substantially match the breath reference within the pre-selected range; and
    (f) a sixth means for comparing the alcohol signal with the alcohol reference and in response generating one of (i) a passing signal if the alcohol signal is less than the threshold level and (ii) a failing signal if the alcohol signal equals or exceeds the threshold level.

2. The apparatus defined in claim 1, further including: a seventh means for retrievably storing the breath signature signal, the alcohol signal, the response of the fifth means in comparing the breath signature signal with the breath reference, the response of the sixth means in comparing the alcohol signal with the alcohol reference, and the date and the time when the breath sample was analyzed.

3. The apparatus defined in claim 1, further including: an eighth means for preventing the use of the apparatus by an unauthorized person.

4. The apparatus defined in claim 1, further including: a ninth means for numerically displaying the alcohol signal and the response of the sixth means in comparing the alcohol signal with the alcohol reference.

5. The apparatus defined in claim 1, further including: a tenth means for displaying a plurality of status indicators regarding the apparatus and the breath sample, the status indicators including a plurality of differently colored lights which variously cycle to being in the states of steady on, flashing on, and steady off.

6. The apparatus defined in claim 1, further including: an eleventh means for supplying power to the apparatus.

7. The apparatus defined in claim 1, further including: a twelfth means for receiving the breath sample comprising:
    (a) a housing form to be grasped in the hand of a person and transported to the mouth of the person who is to deliver the breath sample, the twelfth means defining within itself a hollow chamber for receiving the breath sample; and
    (b) a mouthpiece removably mountable to the housing to be in fluid communication with the chamber, the mouthpiece including an integral trap for removing moisture and particulate matter entrained in the breath sample as the breath sample moves from the person towards the chamber.

8. The apparatus defined in claim 1, further including: a thirteenth means for interlocking the apparatus into a starter system of a powered machine, the thirteenth means being formed to prohibit operation of the starter system unless both (i) the response generated by the fifth means when comparing the breath signature signal with the breath reference is a valid signal and (ii) the response generated by the sixth means when comparing the alcohol signal with the alcohol reference is a passing signal.

9. The apparatus defined in claim 1, further including: a fourteenth means for coupling the apparatus to a powered machine to detect one of (i) the machine is operating and (ii) the machine is not operating.

10. The apparatus defined in claim 1, further including: a fifteenth means for installing the apparatus in a vehicle so the apparatus is accessible for a person to deliver a the breath sample while being sufficiently secure to inhibit tampering with the apparatus by the person.

11. An apparatus having components for analyzing a breath sample delivered by a subject, the apparatus comprising:
    (a) a transducer formed and positioned for sensing at least the temperature, the pressure and the humidity of the breath sample, the transducer in response generating a breath signature signal;
    (b) a sensor formed and positioned for sensing an alcohol concentration level if any carried by the breath sample, the sensor in response generating an alcohol signal;
    (c) a breath reference, representing a valid common range of breath signature signals of at least the temperature, the pressure and the humidity of a plurality of typical breath samples taken from a reference population of subjects;
    (d) an alcohol reference representing a common range of alcohol concentration levels in a typical subject's blood correlated with a common range of alcohol concentration levels contained in the subject's breath sample, the alcohol reference including an alcohol threshold value which one of (i) if not exceeded corresponds to a passing breath sample and (ii) if equaled or exceeded corresponds to a failing breath sample;

(e) a first means for comparing the breath signature signal with the breath reference and providing as an output signal the information that one of (i) the breath sample is valid because the breath signature signal substantially matches the respective corresponding values in the breath reference and (ii) the breath sample is invalid because the breath signature does not substantially match the respective corresponding values in the breath reference; and (f) a second means for comparing the alcohol signal with the alcohol reference and providing as an output signal the information that one of (i) the breath sample is passing because the alcohol signal is less than the alcohol threshold value and (ii) the breath sample is failing because the alcohol signal is equal to or greater than the alcohol threshold value.

12. The apparatus defined in claim 11, wherein the transducer comprises: a thin film of a substantially dielectric material sandwiched between two electrical conductors.

13. The apparatus defined in claim 11, wherein the transducer comprises: a device having sufficient sensitivity to detect a change in one of at least the temperature, the pressure and the humidity resulting from an alteration of the alcohol concentration level carried by the breath sample, the change in one of at least the temperature, the pressure and the humidity exhibiting itself by causing a change in the breath signature signal.

14. The apparatus defined in claim 11, wherein the breath signature signal comprises: a frequency spectrum waveform.

15. The apparatus defined in claim 11, wherein the breath reference comprises: a plurality of frequency spectrum waveforms.

16. The apparatus defined in claim 11, wherein the alcohol reference comprises: a look-up table stored in a computer memory in the form of a plurality of varying percent blood alcohol concentrations correlated with a plurality of measurements of the varying alcohol contents present in a plurality of known breath samples.

17. The apparatus defined in claim 11, wherein the alcohol threshold comprises: a measurement of 0.025% blood alcohol concentration.

18. The apparatus defined in claim 11, wherein the first means for comparing comprises: an electronic filter calibrated one of (i) to pass the breath signature signal as valid if the breath signature signal is substantially similar to the breath reference and to (ii) block the breath signature signal as invalid if the breath signature signal is substantially dissimilar from the breath reference.

19. The apparatus defined in claim 18, wherein the electronic filter further includes: a variable means permitting the filter to be adjusted to define the values of the breath signature signal considered to be substantially similar to and substantially dissimilar from the breath reference.

20. The apparatus defined in claim 11, wherein the valid breath sample comprises: a deep lung breath sample.

21. The apparatus defined in claim 11, further including: an enabling switch, coupled to receive at least the signal from the first comparing means that the breath signal is valid, the enabling switch being coupled to then one of (i) enable the second means for comparing to compare the alcohol signal with the alcohol reference and (ii) not enable the second means for comparing to compare the alcohol signal with the alcohol reference.

22. The apparatus defined in claim 11, further including: a visual display formed for receiving the respective output signals from the first comparing means and the second comparing means and formed for showing a test result generated in response to analyzing a breath sample, the test results including at least (i) the fact that a breath sample was delivered to be analyzed, (ii) the measured numberical value of the percent blood alcohol concentration in the breath sample, and (iii) one of breath sample is passing and failing.

23. The apparatus defined in claim 22, wherein the test results further include: the date and the time of day of delivery of each of the breath samples for analysis.

24. The apparatus defined in claim 11, further including: a memory formed for retreivably storing the plurality of the test results of analyzing all the breath samples.

25. The apparatus defined in claim 11, further including: an electronic controller unit coupled for analyzing the breath sample, and producing, displaying and storing the analysis test results.

26. The apparatus defined in claim 11, further including: an electronic controller unit, coupled to receive the breath signature signal and the alcohol signal, and also coupled to the first comparing means and the second comparing means to control the respective comparisons of the breath signature signal to the breath reference and of the alcohol signal to the alcohol reference.

27. The apparatus defined in claim 11, further including: a sampler unit defining within itself a chamber for receiving the breath sample, the sampler unit being formed to house each of the transducer and the sensor so each is in fluid communication with the chamber.

28. The apparatus defined in claim 27, wherein the sampler unit further includes: a hollow detachable disposable mouthpiece in fluid communication with the chamber, sized to permit the lips of a person to be sealed around the mouthpiece for delivering a breath sample to the chamber, and formed with an integral trap for capturing the moisture and the particulate matter if any entrained in the breath sample.

29. The apparatus defined in claim 28, wherein the sampler unit further includes: a keyboard, mounted to the sampler unit, accessible for finger operation to permit a subject person to input a personal identification number which identifies the subject as the authorized user of the apparatus.

30. The apparatus defined in claim 29, wherein the sampler comprises: an object sized to be hand-held.

31. The apparatus defined in claim 11, further including: a junction box coupled to and operationally interconnecting the apparatus components, the junction box being operable by a microprocessor coupled to control the switching performed by the junction box, for routing the signals between and among the apparatus components.

32. The apparatus defined in claim 11, further including: a switch having at least an inoperable position when not energized and an operable position when energized, the switch being coupled to react at least to the signals that the breath sample is both valid and passing, the switch in response to these signals energizing itself from the normally inoperable position to the energized operable position.

33. The apparatus defined in claim 32, wherein the switch comprises: an ignition switch of a motor-driven vehicle.

34. The apparatus defined in claim 11, further including: a power supply system.

35. The apparatus defined in claim 34, wherein the power supply system comprises:
(a) a rechargeable remote battery of the type used in the electrical system of a motor-driven vehicle, the remote battery being coupled for recharging by the vehicle;
(b) a rechargeable local battery coupled to power the apparatus electronics, and also coupled to the vehicle for recharging; and
(c) a detector means for sensing if the motor is one of (i) in operation and (ii) not in operation, the detector means being coupled to a battery control electronics component which selects one of (iii) a battery charge mode if the motor is in operation and (iv) a non-battery charge mode if the motor is not in operation.

36. The apparatus defined in claim 27, further including: a cradle formed to removably secure the sampler unit in place when not in use.

37. An apparatus for performing a test of a breath sample delivered to a sampler by a person to determine a measure of the alcohol content if any of the breath sample and to determine one of (i) the alcohol content is less than a pre-determined threshold level and thus the breath sample is a passing sample, and (ii) the alcohol content is greater than the threshold level and thus the breath sample is a failing sample, the apparatus being usable without a necessary sequence of operation, the apparatus comprising:
(a) a first means for accurately determining the precise moment for starting the measurement of the alcohol content;
(b) a second means for minimizing tampering with the apparatus by the person to prevent the changing of any test result and to prevent damage to the apparatus;
(c) a third means for providing a hygenic breath sample to the sampler;
(d) a fourth means for easily installing the apparatus to interconnect into the ignition system of a vehicle, the apparatus permitting the ignition system to be started by the person if the person delivers a passing sample and not permitting the ignition system to be started by the person if the person delivers a failing sample;
(e) a fifth means for performing the test quickly so no more than about ten seconds time elapses from the beginning to the end of a test; and
(f) a sixth means for storing the test results to prevent access by the person who delivers the breath sample and to permit access by a person authorized to retrieve the test results.

38. The apparatus defined in claim 37, wherein the first means comprises:
(a) a means for generating a breath signature signal in response to the temperature, the pressure and the humidity of the breath sample;
(b) a means for providing a range of a plurality of breath reference signals representing the average values of the temperature, the pressure and the humidity for a reference population of whom the person is a member; and
(c) a means for comparing the breath signature signal to the breath reference signal and in response generating one of (i) a valid signal if the breath signature signal substantially matches within a pre-selected range the breath reference and (ii) an invalid signal if the breath signature signal does not substantially match the breath reference within the pre-selected range.

39. The apparatus defined in claim 37, wherein the second means comprises:
(a) a means for projecting a light beam through the apparatus; and
(b) means for detecting the interruption of the light beam.

40. The apparatus defined in claim 37, wherein the second means comprises: a means for isolating the apparatus into a plurality of remote components which are not easily accessible to the person delivering the breath sample.

41. The apparatus defined in claim 37, wherein the third means comprises: a disposable mouthpiece, removably mountable to the sampler, the mouthpiece defining within itself a hollow breath passage having an integral trap for removing moisture and particulate matter entrained in the breath sample before the breath sample enters the sampler.

42. A method for analyzing a breath sample, comprising the steps of:
(a) sensing the pressure, the temperature and the humidity of the breath sample and in response generating a breath signature signal;
(b) sensing the alcohol content if any of the breath sample and in response generating an alcohol signal;
(c) providing a breath reference;
(d) providing an alcohol reference which includes an alcohol threshold level;
(e) comparing the breath signature signal with the breath reference and in response generating one of (i) a valid signal if the breath signature signal substantially matches within a pre-selected range the breath reference and (ii) an invalid signal if the breath signature signal does not substantially match the breath reference within the pre-selected range; and
(f) comparing the alcohol signal with the alcohol reference and in response generating one of (i) a passing signal if the alcohol signal is less than the threshold level and (ii) a failing signal if the alcohol signal equals or exceeds the threshold level.

43. The method defined in claim 42, further including the step of: retrievably storing the breath signature signal, the alcohol signal, the response of the step of comparing the breath signature signal with the breath reference, the response of the step of comparing the alcohol signal with the alcohol reference, and the date and the time when the breath sample was analyzed.

44. The method defined in claim 42, further including the step of: preventing the use of the apparatus by an unauthorized person.

45. The method defined in claim 42, further including the step of: numerically displaying the alcohol signal and the response of the step of comparing the alcohol signal with the breath reference.

46. The method defined in claim 42, further including the step of: displaying a plurality of status indicators regarding the apparatus and the breath sample, the status indicators including a plurality of differently colored lights which variously cycle to being in the states of steady on, flashing on, and steady off.

47. The method defined in claim 42, further including the step of: supplying power to the apparatus.

48. The method defined in claim 42, further including the steps of:
   (a) delivering the breath sample into a hollow chamber defined within a housing formed to be grasped in the hand of a person and transported to the mouth of the person who is to deliver the breath sample; and
   (b) removing the moisture and the particulate matter entrained in the breath sample as the breath sample moves from the person towards the chamber.

49. The method defined in claim 42, further including the step of: interlocking the apparatus into a starter system of a powered machine to prohibit operation of the starter system unless both (i) the response generated by the step of comparing the breath signature signal with the breath reference is a valid signal and (ii) the response generated by the step of comparing the alcohol signal with the alcohol reference is a passing signal.

50. The method defined in claim 42, further including the step of: coupling the apparatus to a powered machine to detect one of (i) the machine is operating and (ii) the machine is not operating.

51. The method defined in claim 42, further including the step of: installing the apparatus in a vehicle so the apparatus is accessible for a person to deliver a breath sample while being sufficiently secure inhibit tampering with the apparatus by the person.

52. The apparatus defined in claim 37, wherein the threshold level comprises: an adjustable threshold level.

53. The apparatus defined in claim 37, wherein the elapsed time to perform a test comprises: no more than about 10 seconds.

* * * * *